United States Patent [19]
Slater et al.

[11] Patent Number: 6,007,475
[45] Date of Patent: Dec. 28, 1999

[54] RADIOACTIVE THERAPEUTIC SEEDS

[75] Inventors: Charles R. Slater, Fort Lauderdale; Scott L. Jahrmarkt, Miami Beach; Scott T. Smith, Miami, all of Fla.

[73] Assignee: CNS Technology, Inc., Davie, Fla.

[21] Appl. No.: 09/133,082

[22] Filed: Aug. 12, 1998

[51] Int. Cl.⁶ ............................................. A61N 5/00
[52] U.S. Cl. ................................................... 600/8
[58] Field of Search ............................................. 600/1.8

[56] References Cited

U.S. PATENT DOCUMENTS

| | | | |
|---|---|---|---|
| 3,351,049 | 11/1967 | Lawrence | 128/1.2 |
| 4,323,055 | 4/1982 | Kubiatowicz | 128/1.2 |
| 4,702,228 | 10/1987 | Russell, Jr. et al. | 128/1.2 |
| 4,784,116 | 11/1988 | Russell, Jr. et al. | 128/1.2 |
| 4,891,165 | 1/1990 | Suthanthiran | 252/633 |
| 5,342,283 | 8/1994 | Good | 600/8 |
| 5,405,309 | 4/1995 | Carden, Jr. | 600/3 |
| 5,713,828 | 2/1998 | Coniglione | 600/7 |

*Primary Examiner*—John P. Lacyk
*Attorney, Agent, or Firm*—David P. Gordon; David S. Jacobson; Thomas A. Gallagher

[57] ABSTRACT

Radioactive therapeutic seeds include a two part seed capsule, a radioactive isotope, and, preferably, a radiopaque marker. According to the invention, the seed capsule has an outer part, and an inner part which fits into the outer part and which carries the radioactive isotope. The capsule is sealed by welding the end(s) of the inner part to the end(s) of the outer part. According to one embodiment, the outer part of the seed capsule is a cylinder with one open end and one closed end. The inner part of the seed capsule has a reduced diameter portion which carries the isotope and a larger diameter portion which mates with the open end of the cylinder. According to another embodiment, the outer part of the seed capsule is a cylinder with two open ends. The inner part has a reduced diameter portion which carries the isotope and two larger diameter portions which mate with the open ends of the cylinder. According to some embodiments of the invention, the isotope is carried on a radiopaque structure which is mounted on the reduced diameter portion of the inner part of the seed capsule. According to another embodiment, the inner part of the seed capsule is a hollow member. According to another embodiment, the inner part of the seed capsule is made of radiopaque material.

10 Claims, 2 Drawing Sheets

RADIOACTIVE THERAPEUTIC SEEDS

BACKGROUND OF THE INVENTION

1. Field of the Invention

The invention relates to radioactive therapeutic seeds. More particularly, the invention relates to improved radioactive therapeutic seeds for the treatment of oncological and other medical conditions.

2. State of the Art

Radioactive seed therapy is a well known and well accepted medical procedure for the treatment of various oncological and other medical conditions. Seed therapy, also known as brachytherapy typically involves the implantation of fifty to one hundred tiny capsules (seeds) into or around a treatment site. The capsules contain a radioactive isotope which irradiates the treatment site at close range without adversely affecting other parts of the body. Brachytherapy has been used successfully in the treatment of various types of cancers such as prostate cancer. It has also been used to prevent the growth or regrowth of tissues in the treatment of various occlusive diseases such as arteriosclerosis and arthrosclerosis subsequent to balloon angioplasty.

Radioactive therapeutic seeds are carefully designed to possess several important qualities. First, they must be relatively small, approximately 0.025 inch in diameter and approximately 0.16 inch long so that they may be implanted using minimally invasive instruments and techniques. Second, the radioactive isotope must be enclosed in a biocompatible protective package since the seeds are typically not removed and will remain in the body for many years. Third, each seed should preferably include a radiopaque marker so that it can be located at the treatment site with the aid of fluoroscopy. Fourth, the protective package and the radiopaque marker preferably do not cast "shadows" in the irradiation pattern of the isotope. Fifth, the isotope should be evenly distributed within the protective package so as to avoid any "hot spots" of radiation.

The state of the art of radioactive therapeutic seeds is substantially disclosed in seven U.S. Pat. No. 5,713,828 to Coniglione for "Hollow-Tube Brachytherapy Device", U.S. Pat. No. 5,405,309 to Carden, Jr. for "X-Ray Emitting Interstitial Implants", U.S. Pat. No. 4,891,165 to Suthanthiran for "Device and Method for Encapsulating Radioactive Materials" and U.S. Pat. No. 4,784,116 to Russell, Jr. et al. for "Capsule for Interstitial Implants", U.S. Pat. No. 4,702,228 to Russell, Jr. et al. for "X-Ray Emitting Interstitial Implants", U.S. Pat. No. 4,323,055 to Kubiatowicz for "Radioactive Iodine Seed", and U.S. Pat. No. 3,351,049 to Lawrence for "Therapeutic Metal Seed Containing within a Radioactive Isotope Disposed on a Carrier and Method of Manufacture".

The Lawrence patent, which issued in 1967, describes many of the essential features of radioactive therapeutic seeds. Lawrence describes radioactive isotopes (I-125, Pd-103, Cs-131, Xe-133, and Yt-169) which emit low energy X-rays and which have relatively short half-lives. When implanted at a treatment site, these isotopes provide sufficient radiotherapy without posing a radiation danger to the medical practitioner(s), people in the vicinity of the patient, or other parts of the patient's body. Lawrence further describes a protective capsule which contains the isotope and prevents it from migrating throughout the body where it might interfere with healthy tissue. The capsule is cylindrical and made of low atomic number biocompatible materials such as stainless steel or titanium which do not absorb X-rays. The isotope is coated on a rod shaped carrier made of similar X-ray transparent material and is placed inside the capsule cylinder. The ends of the capsule cylinder are closed by swaging or spinning and soldering or welding. According to a preferred embodiment, Lawrence places a radiopaque marker inside the seed. In one embodiment, the marker is a wire embedded inside the carrier rod. The wire is made of high atomic number material such as gold or tungsten which absorb X-rays.

In 1980, Kubiatowicz made a minor improvement in the basic Lawrence design by providing that the entire isotope carrier be made of radiopaque material such as silver. Kubiatowicz recognized that since the isotope was carried on the entire outer surface of the carrier, there was no need to make the carrier body X-ray transparent as suggested by Lawrence. The larger radiopaque carrier body described by Kubiatowicz makes the seeds easier to see with X-ray or fluoroscopic examination. Thus, the seeds may be placed more accurately at/around the treatment site.

Several years later, Russell, Jr. et al., in U.S. Pat. Nos. 4,707,228 and 4,784,116, explained that the capsule design of Lawrence and Kubiatowicz produces anisotropic angular radiation distribution. According to Russell, Jr. et al., the shell forming techniques used in the Lawrence-type seeds results in large beads of shell material at the ends of the seeds. These beads substantially shield radiation thereby casting shadows in the irradiation pattern of the isotope. Russell, Jr. et al. proposed a new seed design to solve this problem. In particular, Russell, Jr. et al. proposed a seed having a cylindrical container which is sealed with end caps which have a wall thickness that is substantially the same as the wall thickness of the cylindrical container. The end caps are attached to the cylindrical container by welding or crimping.

An alternate solution to the non-uniform radiation pattern of the Lawrence type seeds was proposed by Suthanthiran in U.S. Pat. No. 4,891,165. Suthanthiran's solution was to form a seed capsule from two interfitting sleeves, each having one open end and one closed end. The thickness of the sleeve side walls and their closed ends is such that when the sleeves are interfitted the total side wall thickness of the assembled capsule is approximately equal to the end wall thickness.

Other improvements in radioactive therapeutic seeds are disclosed in U.S. Pat. No. 5,405,309 which concerns a safe isotopically pure Pd-103 seed, and U.S. Pat. No. 5,713,828 which concerns a hollow tube seed which can be implanted with suture material.

Despite the fact that radioactive therapeutic seeds have been in use for over thirty years and despite the several significant improvements made in these seeds, many concerns still exist regarding their design and construction.

While significant attention has been given to the methods by which a cylindrical seed capsule is sealed, it is still difficult to seal the ends of such a small cylindrical capsule without adversely affecting the functionality of the seed. For example, most of the proposed solutions to the end shadow problem of the Lawrence type seed are difficult to implement. The seeds are manually assembled under a microscope and fitting small pieces together is always difficult.

SUMMARY OF THE INVENTION

It is therefore an object of the invention to provide radioactive therapeutic seeds which are easy to manufacture.

It is also an object of the invention to provide radioactive therapeutic seeds which have sealed ends which do not significantly interfere with the irradiation pattern of the seed.

It is also an object of the invention to provide methods for manufacturing radioactive therapeutic seeds which achieve the aforementioned objects.

In accord with these objects which will be discussed in detail below, the radioactive therapeutic seeds of the present invention include a two part seed capsule, a radioactive isotope, and, preferably, a radiopaque marker. According to the invention, the seed capsule has an outer part, and an inner part which fits into the outer part and which carries the radioactive isotope. The capsule is sealed by welding the end(s) of the inner part to the end(s) of the outer part. According to one embodiment, the outer part of the seed capsule is a cylinder with one open end and one closed end. The inner part of the seed capsule has a reduced diameter portion which carries the isotope and a larger diameter portion which mates with the open end of the cylinder. According to another embodiment, the outer portion of the seed capsule is a cylinder with two open ends. The inner part has a reduced diameter portion which carries the isotope and two larger diameter portions which mate with the open ends of the cylinder. According to some embodiments of the invention, the isotope is carried on a radiopaque structure which is mounted on the reduced diameter portion of the inner part of the seed capsule. According to another embodiment, the inner part of the seed capsule is a hollow member. According to another embodiment, the inner part of the seed capsule is made of radiopaque material.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
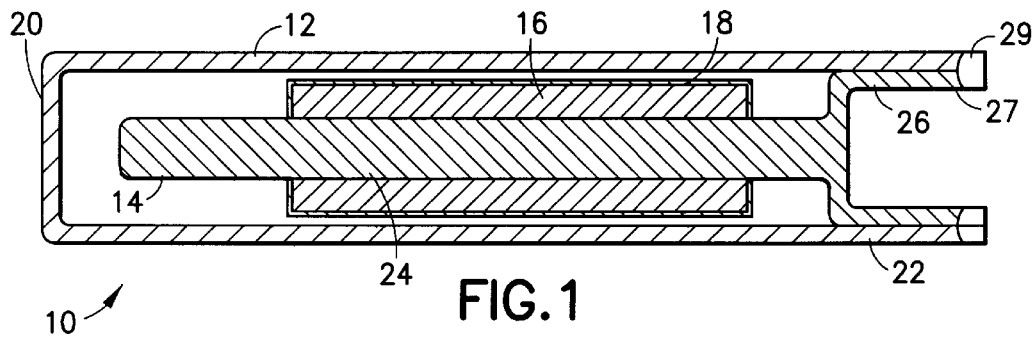
FIG. 1 is an enlarged schematic longitudinal section of a radioactive therapeutic seed according to a first embodiment of the invention.

Referring now to FIG. 1, a radioactive therapeutic seed 10 according to the invention includes an outer cylinder 12, a stepped inner cylinder 14, a radiopaque (e.g. high Z material) marker 16, and a radioactive isotope 18. The outer cylinder 12 and the inner cylinder 14 are made of radiotransparent, radiotranslucent, or low Z material which does not absorb much radiation. The outer cylinder 12 has a substantially constant diameter, a closed end 20, and an open end 22. The stepped inner cylinder 14 has a reduced diameter portion 24 and an enlarged diameter portion 26. The radiopaque marker 16 is a substantially cylindrical member which is mounted on the reduced diameter portion 24 of the stepped inner cylinder 14. The marker 16 is coated with the isotope 18. The enlarged diameter portion 26 of the inner cylinder 14 has an outer diameter which is substantially the same as the inner diameter of the open end of the outer cylinder 12. The seed 10 is sealed by placing the stepped inner cylinder 14 inside the outer cylinder 12 so that the enlarged diameter portion 26 of the inner cylinder 14 engages with the open end 22 of the outer cylinder 12 as shown in FIG. 1. The end 27 of the enlarged diameter portion 26 of the inner cylinder 14 is welded to the open end 22 of the outer cylinder 12 as indicated by reference numeral 29 in FIG. 1. The wall thickness of the outer cylinder 12 is substantially constant and the enlarged diameter portion 26 of the inner cylinder 14 is preferably hollow with a wall thickness comparable to the wall thickness of the outer cylinder. The relative sizes of the outer and inner cylinders facilitate assembly of the seed 10 and permit a substantially isotropic radiation pattern.

Figure 2:
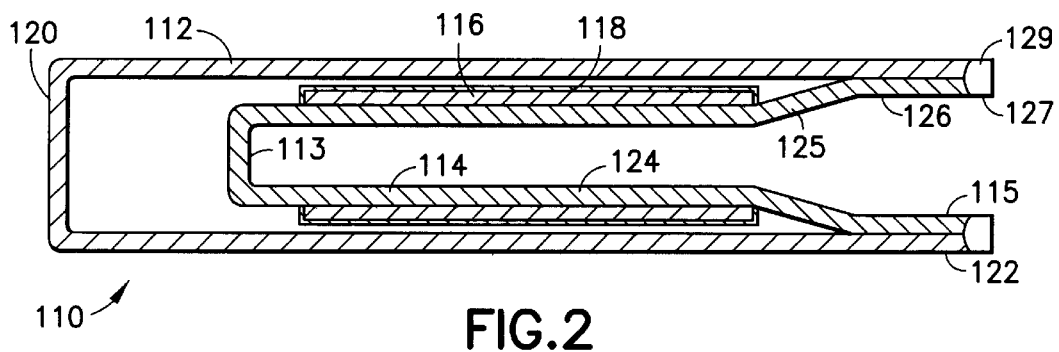
FIG. 2 is an enlarged schematic longitudinal section of a radioactive therapeutic seed according to a second embodiment of the invention.

Turning now to FIG. 2, a second embodiment of a radioactive therapeutic seed 110 according to the invention is similar to the first embodiment described with reference to FIG. 1 and similar reference numerals identify structure which is similar to the first embodiment. According to this embodiment, the inner cylinder 114 is a substantially hollow tapered cylinder having one closed end 113 and one open end 115. The closed end 113 is part of the reduced diameter portion 124 and the open end 115 is part of the enlarged diameter portion 126. The inner cylinder 114 is also provided with a tapered portion 125 which lies in between the small diameter portion 124 and the large diameter portion 126. The seed 110 is assembled in substantially the same way as the seed 10 with the marker 116 surroundign the inner cylinder 114 and the isotope 118 coated on the marker 116. The wall thicknesses of the inner cylinder 114 and the outer cylinder 112 are substantially the same. The relative sizes of the outer and inner cylinders facilitate assembly of the seed 110 and permit a substantially isotropic radiation pattern.

Figure 3:
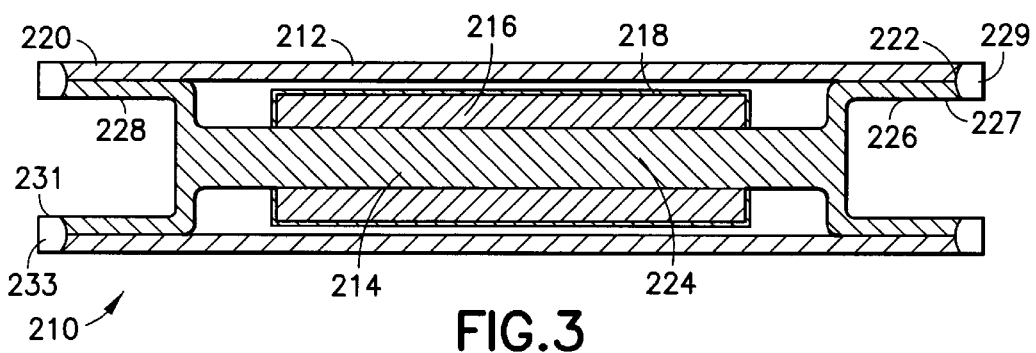
FIG. 3 is an enlarged schematic longitudinal section of a radioactive therapeutic seed according to a third embodiment of the invention.

Another embodiment of a radioactive therapeutic seed according to the invention is shown in FIG. 3. The seed 210 is similar to the first embodiment described with reference to FIG. 1 and similar reference numerals identify structure which is similar to the first embodiment. According to this embodiment, the outer cylinder 212 has two open ends 220, 222 and the stepped inner cylinder 214 has two enlarged diameter portions 226, 228 between which there is the reduced diameter portion 224. The seed 210 is assembled in a manner similar to the assembly of the seeds 10 and 110 described above except that the marker 216 is either molded on the culinder or is provided with a slit (not shown) to permit assembly. The isotope 218 coates the marker 216. It will be appreciated that the two ends 227, 231 of the inner cylinder are welded to the ends 222, 220 of the outer cylinder as shown at 229, 233 in FIG. 3.

Figure 4:
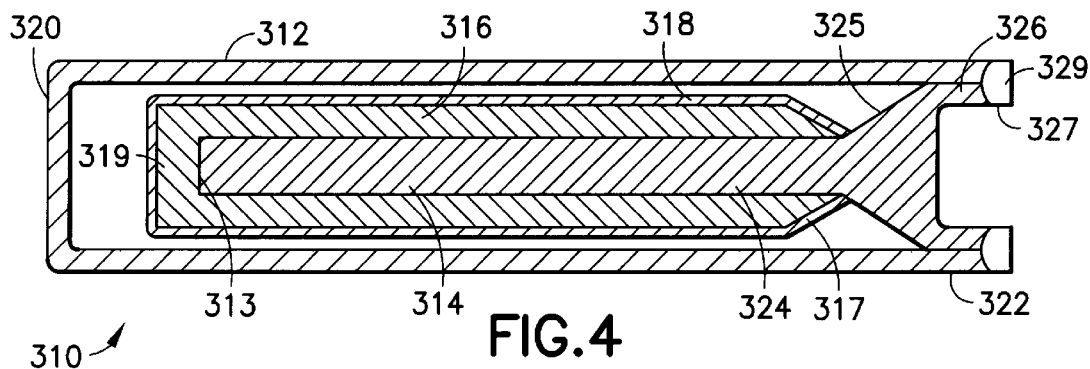
FIG. 4 is an enlarged schematic longitudinal section of a radioactive therapeutic seed according to a fourth embodiment of the invention.

Turning now to FIG. 4, a radioactive therapeutic seed 310 according to the invention is similar to the first embodiment described with reference to FIG. 1 and similar reference numerals identify structure which is similar to the first embodiment. In this embodiment, the tapered inner cylinder 314 has a reduced diameter portion 324, and enlarged diameter portion 326, and a tapered portion 325 therebetween. Substantially all of the reduced diameter portion 324 is covered with a radiopaque marker material 316 including the end 313 of the reduced diameter portion which is covered at 319 by the marker material 316. In addition, a portion 317 of the marker material flares outward from the intersection of the reduced diameter part 314 and the tapered part 325. The marker material 316 thereby assumes the shape of a regular cylinder with a frustoconical end at 317. The marker material 316 is coated with radioactive isotope 318 and the isotope thus assumes a cylindrical configuration with frustoconical end. This arrangement of marker material and isotope provides a nearly perfect isotropic radiation pattern.

Figure 5:
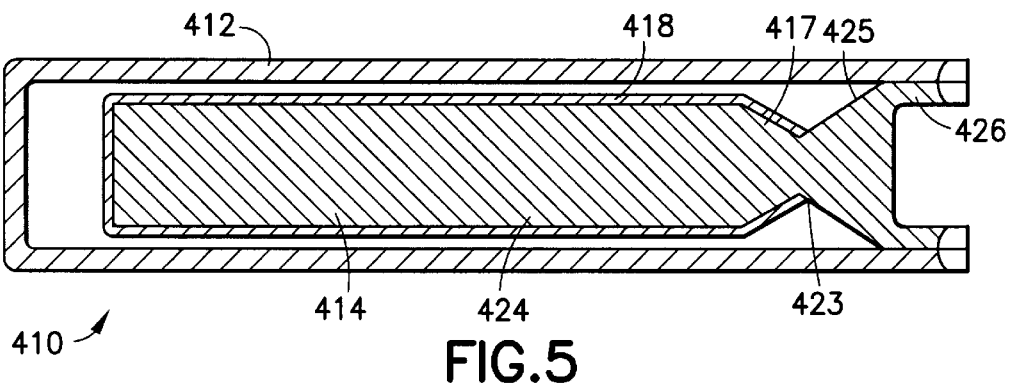
FIG. 5 is an enlarged schematic longitudinal section of a radioactive therapeutic seed according to a fifth embodiment of the invention.

Referring now to FIG. 5, the seed 410 is similar to the seed 310 described above with reference to FIG. 4, and similar reference numerals identify structure which is similar to the structure of seed 310. In this embodiment, the inner cylinder 414 is radiopaque and assumes the general configuration of the combined cylinder 314 and marker material 316 in FIG. 4. More particularly, the cylinder 414 has a reduced diameter portion 424, a larger diameter portion 426, and a narrow waist portion 423 therebetween. The waist portion 423 is defined by a tapered portion 425 and a flared portion 417 as shown in FIG. 5. Radioactive isotope 418 covers all of the reduced diameter portion 424 and flared portion 417 of the cylinder 414, but does not cover the larger diameter portion 426 or the tapered portion 425. This arrangement of isotope and geometry of inner cylinder provides a nearly perfect isotropic radiation pattern.

There have been described and illustrated herein several embodiments of a radioactive therapeutic seed. While particular embodiments of the invention have been described, it is not intended that the invention be limited thereto, as it is intended that the invention be as broad in scope as the art will allow and that the specification be read likewise. For example, those skilled in the art will appreciated that certain features of one embodiment may be combined with features of another embodiment to provide yet additional embodiments. It will therefore be appreciated by those skilled in the art that yet other modifications could be made to the provided invention without deviating from its spirit and scope as so claimed.

We claim:

1. A radioactive therapeutic seed, comprising:
   a) a substantially cylindrical outer member having a first open end;
   b) a substantially cylindrical inner member having a small diameter portion and a first large diameter portion, said first large diameter portion in mating engagement with said first open end; and
   c) a radioactive isotope carried on said small diameter portion.

2. A seed according to claim 1, further comprising:
   d) a radiopaque marker material disposed on said small diameter portion, said isotope being disposed on top of said marker material.

3. A seed according to claim 1, wherein:
   said first large diameter portion is welded to said first open end.

4. A seed according to claim 1, wherein:
   said inner member is substantially hollow.

5. A seed according to claim 1, wherein:
   said outer member has a second open end,
   said inner member has a second large diameter portion with said small diameter portion being located between said first and second large diameter portions, and
   said second large diameter portion being in mating engagement with said second open end.

6. A seed according to claim 5, wherein:
   said first large diameter portion is welded to said first open end, and
   said second large diameter portion is welded to said second open end.

7. A seed according to claim 1, wherein:
   said inner member has a tapered portion located between said small diameter portion and said first large diameter portion.

8. A seed according to claim 4, wherein:
   said inner member has a tapered portion located between said small diameter portion and said first large diameter portion.

9. A seed according to claim 1, wherein:
   said inner member is radiopaque.

10. A seed according to claim 1, wherein:
    said inner member has a narrow waist portion located between said small diameter portion and said first large diameter portion,
    said narrow waist portion being defined by adjacent tapered and flared portions.

* * * * *